United States Patent [19]
Henderson et al.

[11] Patent Number: 6,066,175
[45] Date of Patent: May 23, 2000

[54] FUSION STABILIZATION CHAMBER

[76] Inventors: Fraser C. Henderson; Rebecca Sasscer Henderson, both of 6705 S. Osborne Rd., Upper Marlboro, Md. 20772; John W. Newman, 27 Paper Mill Rd., Newtown Square, Pa. 19073

[21] Appl. No.: 09/095,418

[22] Filed: Jun. 9, 1998

Related U.S. Application Data

[63] Continuation-in-part of application No. 08/891,513, Jul. 11, 1997, abandoned, which is a continuation of application No. 08/539,600, Oct. 5, 1995, abandoned, which is a continuation-in-part of application No. 08/328,585, Oct. 24, 1994, abandoned, which is a division of application No. 08/018,373, Feb. 16, 1993, Pat. No. 5,405,391.

[51] Int. Cl.$^7$ .................................................. A61F 2/44
[52] U.S. Cl. ........................................................ 623/17.11
[58] Field of Search ............................................. 623/17

[56] References Cited

U.S. PATENT DOCUMENTS

| | | |
|---|---|---|
| 1,357,714 | 11/1920 | Lane . |
| 2,454,680 | 11/1948 | Stephens . |
| 2,638,302 | 5/1953 | Reed . |
| 3,947,191 | 3/1976 | Milner . |
| 4,309,777 | 1/1982 | Patil . |
| 4,484,570 | 11/1984 | Sutter et al. . |
| 4,501,269 | 2/1985 | Bagby . |
| 4,553,273 | 11/1985 | Wu . |
| 4,554,914 | 11/1985 | Kapp et al. . |
| 4,599,086 | 7/1986 | Doty . |
| 4,636,217 | 1/1987 | Ogilvie et al. . |
| 4,657,550 | 4/1987 | Daher . |
| 4,743,256 | 5/1988 | Brantigan . |
| 4,820,305 | 4/1989 | Harms et al. . |
| 4,863,476 | 9/1989 | Shepperd . |
| 4,878,915 | 11/1989 | Brantigan . |
| 4,932,975 | 6/1990 | Main et al. . |
| 4,955,908 | 9/1990 | Frey et al. . |
| 4,961,740 | 10/1990 | Ray et al. . |
| 5,002,576 | 3/1991 | Fuhrmann et al. . |
| 5,015,247 | 5/1991 | Michelson . |
| 5,059,193 | 10/1991 | Kuslich . |
| 5,236,460 | 8/1993 | Barber . |
| 5,281,226 | 1/1994 | Davydov . |
| 5,290,312 | 3/1994 | Kojimoto et al. . |
| 5,397,364 | 3/1995 | Kozak et al. . |
| 5,405,391 | 4/1995 | Henderson et al. . |
| 5,609,635 | 3/1997 | Michelson . |
| 5,888,223 | 3/1999 | Bray ............................................ 623/17 |

FOREIGN PATENT DOCUMENTS

| | | | |
|---|---|---|---|
| 0179695 | 4/1986 | European Pat. Off. . | |
| 0322334 | 6/1989 | European Pat. Off. . | |
| 0526682 | 2/1993 | European Pat. Off. . | |
| 0 563 503 A1 | 10/1993 | European Pat. Off. | ................. 623/22 |
| 2 651 995 A1 | 3/1991 | France | ..................................... 623/22 |
| 2 704 747 A1 | 11/1994 | France | ..................................... 623/19 |
| 2 727 005 A1 | 5/1996 | France | ..................................... 623/17 |
| 32 05 526 A1 | 9/1983 | Germany | ................................ 623/22 |
| 4114644 | 4/1992 | Japan . | |
| 2004218 C1 | 12/1993 | Russian Federation | ................. 623/17 |
| 1175464 | 8/1985 | U.S.S.R. . | |
| 1739989 | 6/1992 | U.S.S.R. . | |
| 8707827 | 12/1987 | WIPO . | |
| 9501763 | 1/1995 | WIPO . | |

OTHER PUBLICATIONS

"Modular Segmental Spinal—Instrumentation" distr. by Fehling Medizintechnik GmbH.

*Primary Examiner*—David H. Willse
*Attorney, Agent, or Firm*—William H. Eilberg

[57] ABSTRACT

A fusion stabilization chamber stabilizes the spine following removal of one or more vertebrae, and facilitates bone growth. The chamber includes two hollow members, preferably having slightly trapezoidal cross-sections, which slide relative to each other in a telescoping manner. The hollow members preferably have walls made of a metal mesh. Barrel vaults attached to the hollow members form guides for screws which can attach the chamber to the vertebrae adjacent the corpectomy site. Because of its adjustability, the chamber can fit a wide variety of corpectomy sites. One can fill the chamber with bone material, which can eventually fuse to the adjacent bone. A pair of stabilizing plates prevents the surgeon from pushing the chamber too far towards the spinal cord. The chamber eliminates the need to maintain a large and costly inventory of screws, and neurosurgeons can learn to use it quickly and easily. In another embodiment, the device is formed in one non-telescoping piece. An end portion of the hollow member includes a curved flange which corresponds to the curvature of adjacent bone, and a notch which facilitates engagement with such bone. The device can be made in different sizes, so that it can replace relatively large vertebral bodies, as well as relatively small intervertebral discs.

6 Claims, 11 Drawing Sheets

FUSION STABILIZATION CHAMBER

CROSS-REFERENCE TO PRIOR APPLICATION

This is a continuation-in-part of Ser. No. 08/891,513, filed Jul. 11, 1997, now abandoned, which is a continuation of Ser. No. 08/539,600, filed Oct. 5, 1995, now abandoned, which is a continuation-in-part of U.S. patent application Ser. No. 08/328,585, filed Oct. 24, 1994, now abandoned, which is a division of Ser. No. 08/018,373, filed Feb. 16, 1993, now U.S. Pat. No. 5,405,391.

BACKGROUND OF THE INVENTION

The present invention relates to the field of neurosurgery, and provides a device which facilitates the implantation of bone into the spine following removal of vertebrae, and which also facilitates the fusion of the implanted bone with the surrounding bone. The invention also includes a method of performing spinal surgery, and in particular, of stabilizing the spine following removal of one or more vertebrae.

Cancer or trauma or degenerative changes can cause parts of the human vertebrae to develop outgrowths or ridges that can touch the spinal cord and cause pain and/or paralysis. Neurosurgeons have developed means of treating such conditions, by removing part of the vertebrae, and, where appropriate, replacing the removed bone with something else. The removal of all or part of a vertebra is called a "corpectomy" or a "vertebrectomy". In some cases, one can replace the bone removed by corpectomy with bone taken from another site on the body of the patient; in other cases, one can obtain bone from a "bone bank". Given the right conditions, the new bone material will fuse to the bone surrounding the corpectomy site, and can become for practical purposes a part of the patient's body. To achieve the desired fusion, one must stabilize the spine so that the bone has time to fuse. The fusion process can take from six weeks to six months.

In performing spinal surgery, one can approach the spine either from the front (anterior) or rear (posterior) sides. The posterior approach has the disadvantage that since the vertebrae lie on the anterior side of the spinal cord, the surgeon must navigate past the spinal cord before reaching the vertebrae, and must take special care not to disturb the spinal cord. Conversely, with the anterior approach, the surgeon does not encounter the spinal cord while en route to the vertebrae. The present invention concerns the anterior approach.

The prior art contains many systems for stabilizing various parts of the spine following surgery. The development of such systems has made it possible to treat certain lesions of the spine aggressively, instead of simply immobilizing them in a brace. The typical external immobilizing device of the prior art comprises the halo vest. The typical internal immobilizing device comprises the Caspar plate, described below.

The Caspar plate system, named after Dr. Wolfhard Caspar, comprises a means for stabilizing the spine after anterior spinal surgery. The Caspar system includes a set of plates which one attaches to the remaining vertebrae surrounding the corpectomy site. In the Caspar procedure, one screws a plate directly onto the spine, the screws approaching within about one or two millimeters of the spinal cord. The Caspar system provides immediate stabilization of the spine following a corpectomy, and in other cases where the spine has become unstable following an accident. The Caspar system also eliminates the need for wearing the very cumbersome halo vest, and eliminates the need to undergo a separate surgical procedure from the rear.

However, the Caspar system also has disadvantages. It requires a large inventory of expensive equipment, including screws and plates of all sizes. The latter expense can represent a formidable obstacle to many medical institutions. Also, one needs to insert the screws through the spine, engaging the posterior cortex. Although one can monitor the position of the screws with an appropriate real-time viewing apparatus, the procedure carries the potential risk of spinal cord injury or laceration of the vertebral artery. When a competent surgeon performs the procedure, these complications rarely occur, but other complications such as loosening of the screws and persistent instability may develop. Moreover, the difficulty of the procedure discourages many surgeons from even attempting the anterior plating procedure.

The Synthes cervical spine locking plate constitutes another anterior plating system of the prior art. In the Synthes system, one inserts a second screw into the head of the anchor screw, thus creating a second affixation of the plate to the vertebrae. Many regard the Synthes system as easier, safer, and faster to use than the Caspar plate system, because the anchor screw does not penetrate the posterior cortex and because one therefore does not need to monitor the precise position of the screw during insertion. However, the Synthes locking plate has less versatility than the Caspar plate, as it provides the ability to fuse only two to three levels of the cervical spine.

Both the Caspar and Synthes systems also have the disadvantage that they do not work well in patients with osteoporosis, rheumatoid arthritis, ankylosing spondylitis, and other conditions of poor bone growth or metabolic bone disease.

Both the Caspar and Synthes systems have additional disadvantages inherent with the use of screws. First, as mentioned above, screws do become loose. If one uses the screws as the primary means of affixing the stabilizing device to the spine of the patient, loosening of the screws represents a major problem. Moreover, the use of screws presents a technical challenge to the surgeon. Correct screw placement requires experience, as well as a large inventory of expensive equipment, as well as imaging devices for monitoring the position of such screws. Also, with screw-based systems of the prior art, the surgeon must create a large opening in the patient, so as to view the screw along its shaft. Such an opening creates additional risks to the patient, such as the risk of injury to vascular structure and to nearby nerves.

In addition to the problem of how to stabilize the spine immediately after performing a corpectomy, vertebral surgery poses problems relating to the replacement of the removed bone. Some systems of the prior art require the use of a bone strut to replace the diseased bone segments removed in surgery. This bone grafting material costs a great deal, and sometimes one cannot obtain enough material when performing multiple vertebrectomies. Furthermore, bone graft material, usually taken from cadavers, has typically been sterilized by radiation, a process believed to weaken or destroy the strength and osteoconductive properties of bone. While it is possible to use other means of sterilization, such as ethylene oxide or freeze drying, it usually turns out that the best bone graft material comes from the patient, because the patient's own bone will likely fuse more rapidly than bone obtained elsewhere. Unfortunately, harvesting such bone consumes substantial time, involves substantial pain to the patient, and presents other risks, such as risk of infection at the harvest site, hemorrhage, and peripheral nerve injury.

The present invention overcomes the disadvantages of the prior art systems described above. First, the invention provides a device which surgeons can learn to use very easily, and which they can insert without intraoperative fluoroscopy or other means of accurately monitoring the position of a device within the body. Most neurosurgeons can use the device of the present invention with instruments already in their possession.

Secondly, the invention provides an adjustable device which can fit a large range of patients. This feature eliminates the need to keep a large inventory of parts in order to accommodate every possible patient.

Thirdly, the device allows one to use the patient's own cancellous bone which one removes during the vertebrectomy, possibly with the addition of further cancellous bone material from an external source. In any event, the invention reduces or eliminates the need to obtain a pelvic bone autograft from the patient.

The device of the present invention also reduces or eliminates the problem of loosening of screws, which can occur with the plating systems of the prior art, and which clearly can cause substantial pain and expense.

SUMMARY OF THE INVENTION

The fusion stabilization chamber of the present invention includes a pair of hollow members, both of which may have a rectangular or slightly trapezoidal cross-section. One of the hollow members slides within the other. Thus, the chamber comprises two telescoping hollow members. Each hollow member includes at least one barrel vault at one end, each barrel vault comprising threaded means for receiving a screw. The barrel vaults are arranged in a mutually oblique manner, such that the screws inserted into the vaults also lie along mutually oblique lines. The hollow members preferably comprise enclosures defined by four walls formed of a metal mesh. The hollow members may also include means for locking the members in a desired position relative to each other.

In using the stabilization chamber described above, the surgeon first removes the diseased portion of vertebra in the usual manner. The surgeon measures the length of the corpectomy site (the length of the space to be filled), and adjusts the length of the chamber accordingly. One may fasten the locking means so that the telescoping chamber maintains its desired position. Then, the surgeon fills the chamber with bone material, such as bone chips obtained from the corpectomy operation itself, or bone material from other sources, and inserts the chamber into the corpectomy site. The surgeon gently taps the device into place, so that it fills most of the corpectomy site, i.e. the space formerly occupied by the removed vertebra. The chamber does not extend all of the way towards the spinal cord, due to the retaining action of a pair of stabilizing plates.

The surgeon then drills holes in the surrounding bone, using the barrel vaults as guides for the drill bit. The surgeon then inserts the screws through the barrel vaults and fastens them to the bone. Due to the orientation of the barrel vaults, the screws lie along mutually oblique paths, reducing the likelihood that the device will become dislodged.

In an alternative embodiment, one can provide threaded holes in the stabilizing plates also, so that additional screws can pass directly through the stabilizing plates and into the surrounding bone.

In another alternative embodiment, the fusion stabilization chamber includes a single member and does not telescope. Like the first embodiment, the single member has an open mesh structure which is filled with bone chips or any bone substitute or bone morphogenetic protein. This embodiment is especially suited for use in filling the space created after removal of an intervertebral disc. The mesh structure also includes flanges which serve to anchor the device and attach it to adjacent vertebrae, and prevent it from contacting the spinal cord, and barrel vaults to facilitate attachment and stabilization of the device. The device can also include a separate top plate which is affixed to the top of the chamber by screws.

In another embodiment, the chamber comprises a single, non-telescoping member which includes an end portion having flanges and screw holes. The flanges are preferably curved so that they correspond to the curvature of the surrounding bone. Also, the flanges and the chamber together define notches which engage edges of adjacent vertebrae when the device is in use. An access hole in the end portion facilitates the filling of the interior of the chamber with bone fragments. The chamber has a trapezoidal cross-section when viewed in each of at least two mutually-orthogonal directions.

The present invention therefore has the primary object of providing an improved method and apparatus for performing spinal surgery, and in particular, for stabilizing the spine following removal of one or more vertebrae.

The invention has the further object of providing a device which promotes bone fusion in addition to providing stabilization of the spine.

The invention has the further object of simplifying the surgical process of stabilizing the spine after performing a corpectomy.

The invention has the further object of reducing the cost and complexity of the equipment needed to practice spinal surgery.

The invention has the further object of reducing the time required for a surgeon to learn to stabilize the spine following a corpectomy.

The invention has the further object of providing an apparatus and method for promoting fusion of bone in a space between adjacent vertebrae, following removal of an intervertebral disc.

Persons skilled in the art will recognize other objects and advantages of the invention, from a reading of the following brief description of the drawings, the detailed description of the invention, and the appended claims.

DETAILED DESCRIPTION OF THE INVENTION

Figure 1:
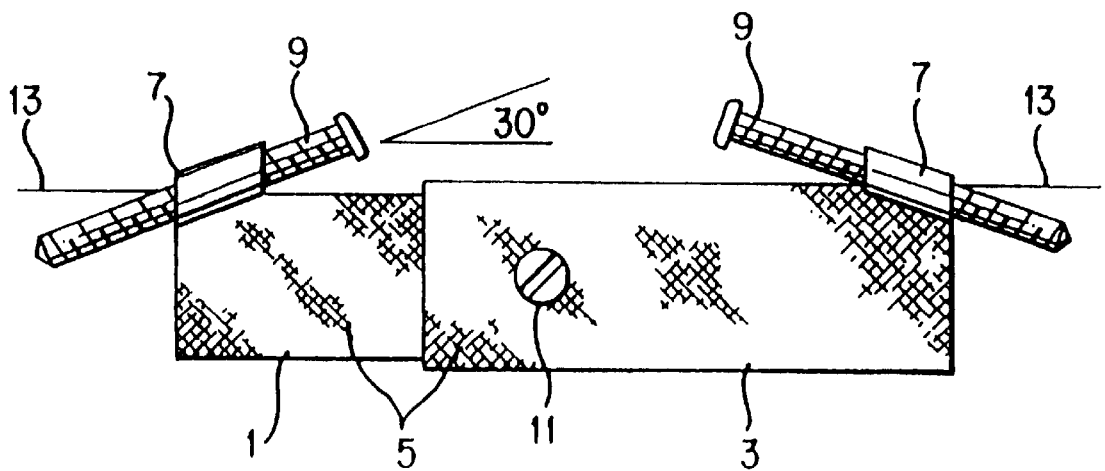
FIG. 1 provides a side elevational view of the fusion stabilization chamber of the present invention.
Figure 2:
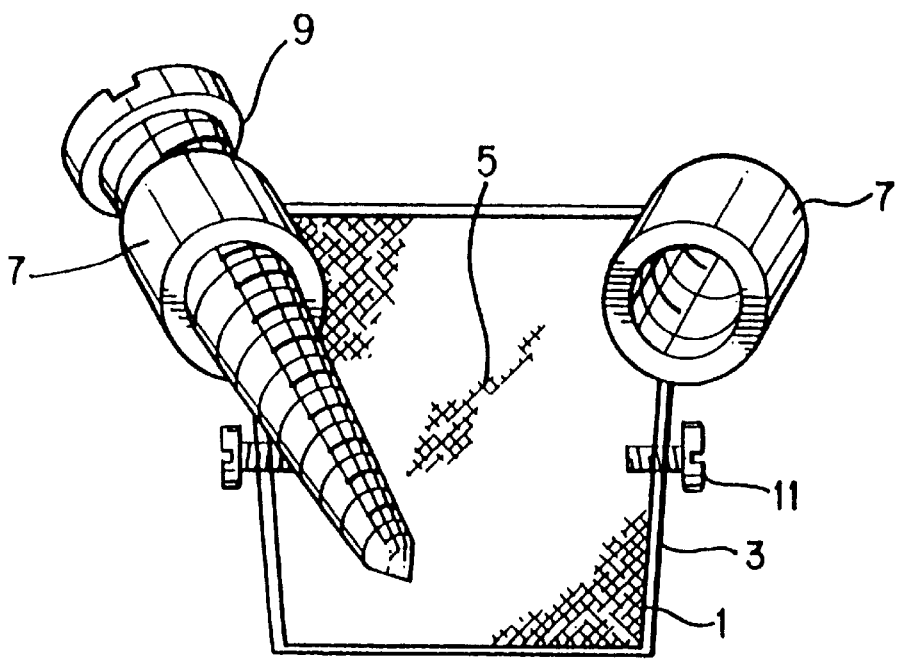
FIG. 2 shows an end view of the stabilization chamber of the present invention.
Figure 3:
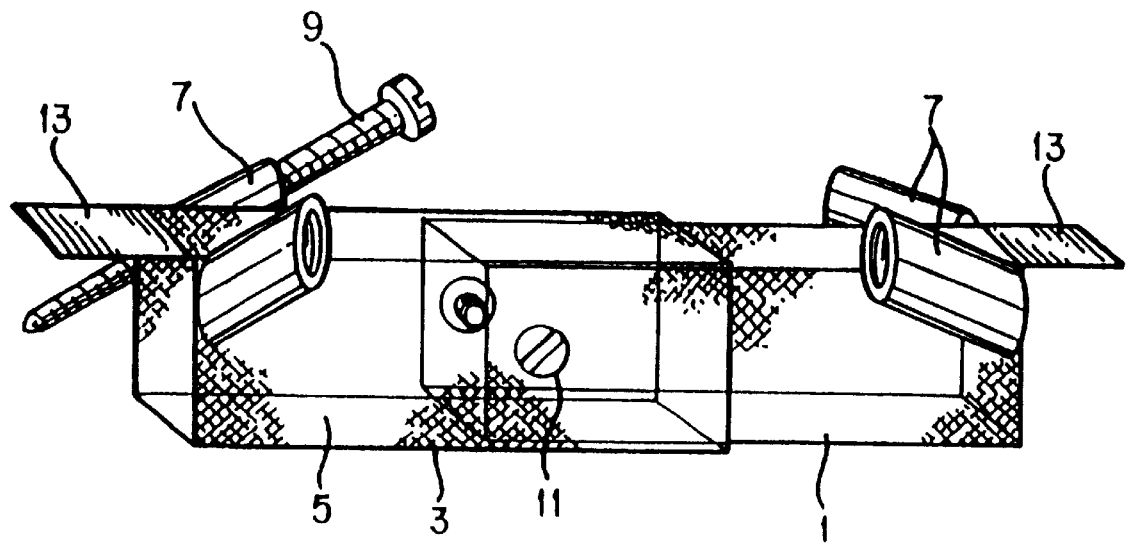
FIG. 3 provides a perspective view of the fusion stabilization chamber.

FIGS. 1–4 show the physical structure of the fusion stabilization chamber of the present invention. The chamber includes first hollow member 1 and second hollow member 3. Both hollow members have a slightly trapezoidal cross-section, as illustrated in the end view of FIG. 2. FIG. 2 exaggerates the trapezoidal shape of the cross-section: in practice, the width of the member might increase by one millimeter for each 15 mm of depth, but one could use other dimensions. Thus, by "slightly trapezoidal", one means that the members are nearly rectangular in cross-section, except for the variation in width described above. The trapezoidal cross-section helps to maintain the chamber in position within the corpectomy site. One inserts the narrower portion of the hollow member into the body cavity first, with the wider portion oriented towards the outside. Thus, the chamber tends to become wedged in its place within the corpectomy site; once pushed in, it becomes difficult to pull out. Although the preferred embodiment includes the trapezoidal cross-section, one can also form the chamber with a perfectly rectangular cross-section, within the scope of the invention.

The first hollow member 1 slides within the second hollow member 3. The members 1 and 3 preferably have walls formed of metal mesh 5. One prefers walls having openings which permit bone growth from the adjacent vertebrae, through the interior of the chamber. However, the walls can have a different construction. They can even comprise solid metal, as bone can fuse to metal. In the latter case, the chamber could be empty.

Figure 4:
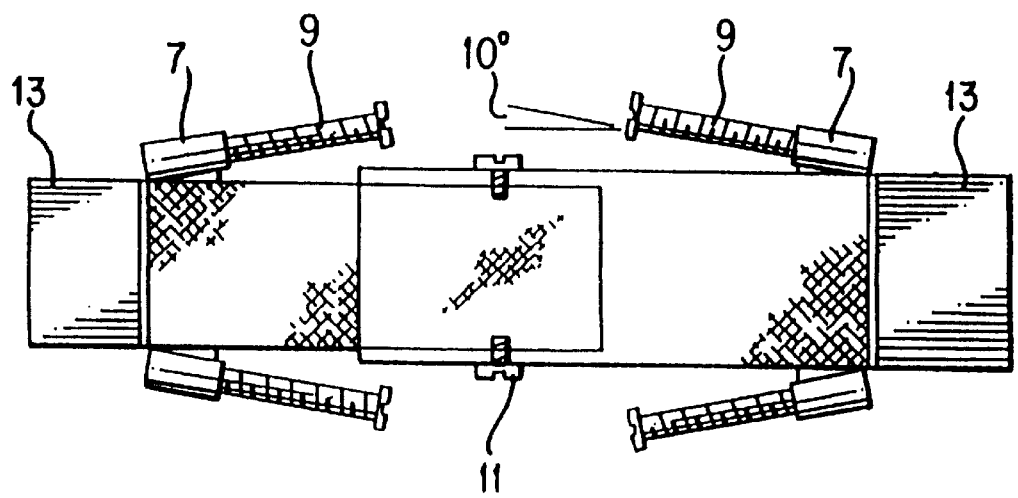
FIG. 4 shows a top view of the stabilization chamber.

In the preferred embodiment, the chamber has two pairs of barrel vaults 7, arranged at the opposite ends of the hollow members. One can vary the number of barrel vaults, within the scope of the invention. The barrel vaults comprise threaded cylinders through which screws 9 pass. FIG. 1 shows that the screws form an angle of about 30° relative to the top longitudinal axis of the chamber. FIG. 4 shows that the screws also form an angle of about 10° relative to the sides of the chamber. One can vary these angles; one should not consider the invention limited to particular angles. In general, one selects angles which enable the screws to pass through the greatest possible thickness of bone, above and below the corpectomy site, and to provide an angle which, from the perspective of the surgeon, facilitates insertion of the screws without the need to make a larger or additional incision.

As shown in the Figures, the barrel vaults comprise mutually oblique members. The screws become self-locking in the barrel vaults. One can also provide an adjustable hexagonal head screwdriver to facilitate tightening of the screws from any angle.

Locking screw 11 holds the first and second hollow members in place. The locking screw thus permits adjustment of the size of the chamber. One slides the hollow members until the chamber has the desired length, and then fixes the selected length by tightening the locking screw.

Figure 5:
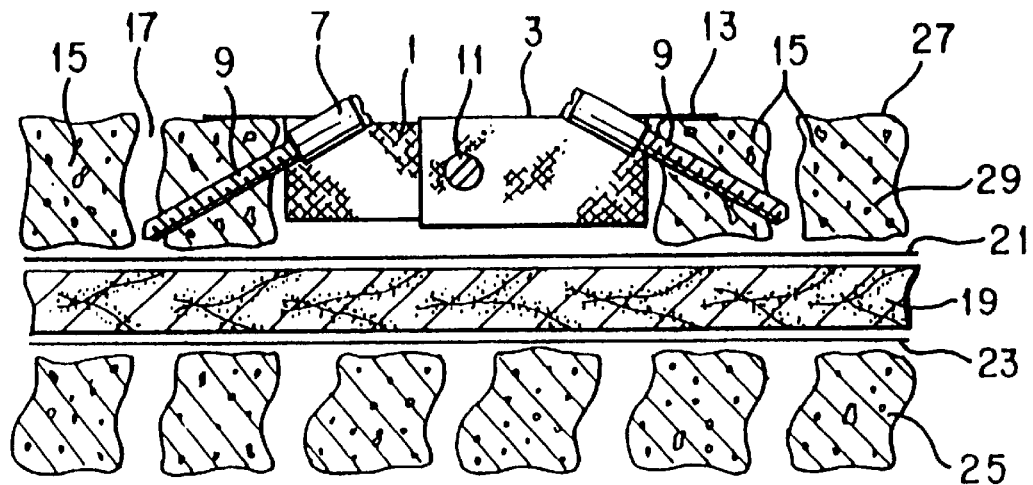
FIG. 5 provides a diagrammatic view showing the fusion stabilization chamber inserted into a corpectomy site.

FIG. 5 provides a diagram of the fusion stabilization chamber inserted into a corpectomy site. The figure shows vertebrae 15, the spaces 17 between adjacent vertebrae representing intervertebral discs. Each vertebra includes an outer bony layer, or cortex 27, which surrounds cancellous material 29 inside. FIG. 5 also shows spinal cord 19, and the structures adjoining the spinal cord, including the posterior longitudinal ligament 21, the ligamentum flavum 23, and the posterior spinous processes 25. As shown in the figure, one has removed several vertebrae, and has inserted the chamber into the resulting empty space.

Stabilizing plates 13 extend from both hollow members, as shown in the Figures. The stabilizing plates serve several purposes. First, as illustrated in FIG. 5, the stabilizing plates keep the chamber at an appropriate depth, preventing the chamber from touching spinal cord 19 or the ligaments surrounding it. By making the depth of the chamber less than the depth of the adjacent vertebrae, one prevents the chamber from coming too close to the spinal cord.

Secondly, the stabilizing plates tend to distribute the bending loads experienced by the chamber, and divert part of these loads away from the screws. As the vertebrae flex back and forth, the stabilizing plates tend to oppose some of the vertebral movement, and absorb some of the tension, thereby tending to prevent the screws from loosening or breaking.

Thirdly, the stabilizing plates help to rigidify the joints formed between the ends of the chamber and the respective adjacent vertebrae. Keeping these joints rigid facilitates the growth of blood vessels from the adjacent vertebrae, through the holes in the chamber walls, and into the bone material within the chamber.

Figure 6:
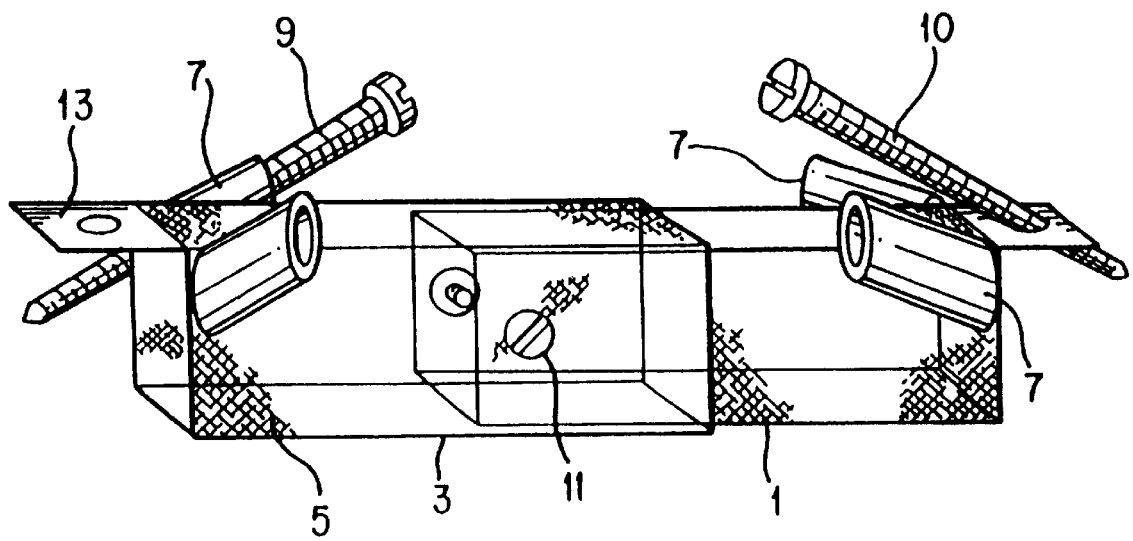
FIG. 6 provides a perspective view of an alternative embodiment of the invention, wherein additional screws pass directly through the stabilizing plates.

FIG. 6 shows, in a perspective view, an alternative embodiment wherein a third screw passes through a threaded hole in each stabilizing plate, in addition to the pair of screws inserted through the associated barrel vaults. FIG. 6 shows additional screw 10 inserted through the stabilizing plate on the right-hand side. The figure does not show the corresponding additional screw on the other side, in order to show the hole in the stabilizing plate, but in practice a similar additional screw 10 would normally be provided. However, one should consider each screw as optional, since it is possible to affix the chamber to the adjacent bone using fewer than all of the available screws.

One would use the embodiment of FIG. 6 in cases where the bone has become weakened. In rare cases, one might even attach the chamber only with the stabilizing plate screws, without any barrel vault screws. In all of the embodiments wherein one provides a threaded hole in the stabilizing plate, the holes should have low "profiles", so that the material defining the plate does not project significantly beyond the plane of the plate.

In using the chamber of the present invention, the surgeon begins by performing a corpectomy in the conventional manner. Immediately after removal of one or more vertebrae, the surgeon measures the length of the corpectomy site with calipers, and adjusts the length of the chamber to make it conform to the length of the corpectomy site. One adjusts the length of the chamber by pulling the hollow members 1 and 3 away from each other or pushing them together, as needed. Then one tightens the locking screw 11 to fix the length (and thus the volume) of the chamber.

Next, the surgeon fills the chamber with bone. The bone can comprise bone chips obtained from the vertebrae removed in the corpectomy procedure, or it can comprise cancellous bone obtained from another site. One might also use a biocompatible osteogenic polymer.

In a variation of the latter step, the surgeon may place bone chips, obtained from the corpectomy, into the chamber, while the corpectomy progresses. However, in this case, one would still need to adjust the chamber to fit the corpectomy site, and one would also need to insure that the bone has substantially filled the volume of the chamber after adjustment of the size of the chamber.

The surgeon then inserts the bone-filled chamber into the corpectomy site, and gently taps it into place, such that the stabilization plates 13 come to rest on the vertebrae immediately adjacent to the corpectomy site. The chamber should fit tightly within the corpectomy site. One may take a lateral spine X-ray to insure that the chamber has seated itself properly in the corpectomy site.

Next, the surgeon drills holes into the adjacent vertebrae, using an appropriate drill, such as a 2 mm twist drill. The barrel vaults 7 form guides for the drill bit, and thereby determine the direction of the holes. The orientation of the barrel vaults unambiguously determines the orientation of the holes. The holes therefore make the same angles as the barrel vaults, relative to the axes of the chamber.

The surgeon then threads the screws 9 into the barrel vaults 7. The barrel vaults direct the screws along the correct path. Due to the interaction of the heads of screws 9 with the barrel vaults, the barrel vaults also insure that the screws 9 become inserted to the correct depth. When tightened, the screws 9 tend to draw the adjacent vertebrae towards the chamber. Note also that the screws pass twice through the cortex of the vertebrae. In other words, each screw has a length sufficient to pass through the cortex 27 at one surface of the vertebra, then through the cancellous material 29 at the core of the vertebra, and again through the cortex as the screw exits the vertebra. Fastening the screws in this manner minimizes the likelihood that the screws will become dislodged.

Following the tightening of the screws, one can take a lateral X-ray to verify proper placement of the screws. If all is correct, one can then close the wound in the conventional manner.

The present invention has many advantages, as outlined below:

1. The fusion stabilization chamber does not rely on screws as the sole means of stabilizing the spine following surgery. Due to the trapezoidal cross-section of the chamber, the chamber becomes firmly wedged within the corpectomy site even before attachment of the screws.

2. The surgeon can learn to insert the fusion stabilization chamber much more quickly than devices of the prior art. Since the barrel vaults automatically determine the direction and depth of the screws, the surgeon will be less likely to make mistakes while using the present invention, and the invention therefore is less intimidating to the surgeon than devices of the prior art. In particular, the oblique direction of the screws lessens the potential damage to the spinal cord. Moreover, most neurosurgeons can use the fusion stabilization chamber with instruments already in their possession.

3. The oblique direction of the screws has the added benefit that it increases the compression effect, by drawing vertebrae above and below the chamber into firm contact with the chamber. Such compression speeds fusion of the bone.

4. The oblique direction of the screws has the additional advantage of reducing the required size of the surgical incision, because the surgeon can reach deeply into adjacent vertebrae, using the screws, without exposing those vertebrae.

5. Because of the ease and manner of insertion of the device, the surgeon need not use intraoperative fluoroscopy, or other monitoring means, while inserting the device.

6. The present invention eliminates the need for a large inventory of stabilization plates and screws for fitting different sizes of vertebrae. One can construct the present invention in two or three basic sizes, which together fit virtually all possible corpectomy sites, due to the telescoping feature of the chamber. Thus, the invention reduces the cost of maintaining an inventory of materials. Moreover, due to the simple structure of the fusion stabilization chamber, one can manufacture it relatively inexpensively.

7. One can make the fusion stabilization chamber of strong titanium metal mesh which allows bone to grow from end to end and from side to side. One can easily fill the chamber with the patient's own cancellous bone mixed with hydroxyapatite crystals and/or other biocompatible synthetic bone substitutes known to increase the rate of bone formation. Thus, the present invention reduces the need to harvest bone from other sites on the patient's body.

8. The structure of the fusion stabilization chamber provides stability through all three degrees of freedom of movement.

In an alternative embodiment, one can replace the locking screw with a screw device located inside the chamber and extending along the entire length of the chamber. Thus, the latter screw device would comprise a type of jack. Turning the latter screw would vary the overall length of the jack, which is equivalent to varying the length of the chamber. With this arrangement, one need not adjust the length of the chamber before inserting it into the corpectomy site. Instead, one would first insert the chamber, and then turn the screw to adjust the jack, until the chamber becomes long enough to occupy the entire space. The above-described screw device would then comprise the means for locking the hollow members into a fixed position relative to each other, and could be used instead of, or in addition to, locking screw 11. One would use a bevel gear, or equivalent mechanical device, for adjusting the jack while the chamber is in position. The latter alternative should be considered within the scope of the present invention.

In another alternative embodiment, one can coat the outside of the chamber with an osteoconductive substance, such as hydroxyapatite, or the like, to promote fusion of the chamber to the surrounding bone. This coating can be instead of, or in addition to, the filling of the chamber with bone material. The invention should be considered to include the latter alternatives.

The chamber used in the present invention can have various cross-sections. The invention is not limited to the rectangular or trapezoidal cross-sections discussed above, but can include other shapes. For example, one could form the chamber with a circular cross-section, in which case the chamber would have the general shape of a cylinder.

Figure 7:
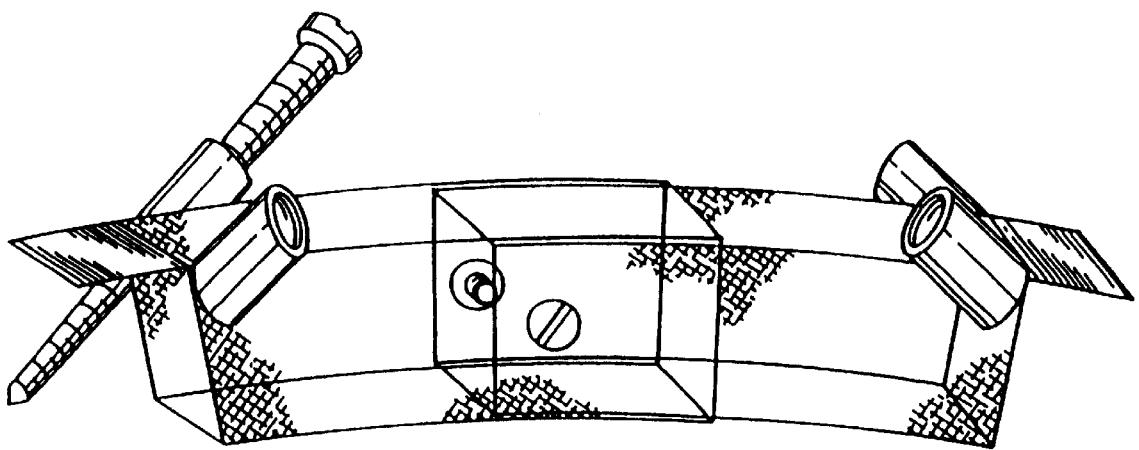
FIG. 7 provides a perspective view, similar to that of FIG. 3, showing an embodiment in which the fusion stabilization chamber is curved to fit the curvature of the spine.

The present invention is also not limited to a chamber having straight walls. Instead, the chamber could be curved along its length, as shown in FIG. 7. In this way, one can make the chamber fit the curvature of the spine. In the latter case, both hollow members would be curved, so that they could slide back and forth within each other, while maintaining the desired curvature. This embodiment would be useful for a corpectomy which spans a relatively large number of vertebrae.

The bone chips used in the present invention could be replaced by a bone substitute material, or a bone-forming substrate with bone morphogenic proteins, or some combination of any of the above.

Figure 8:
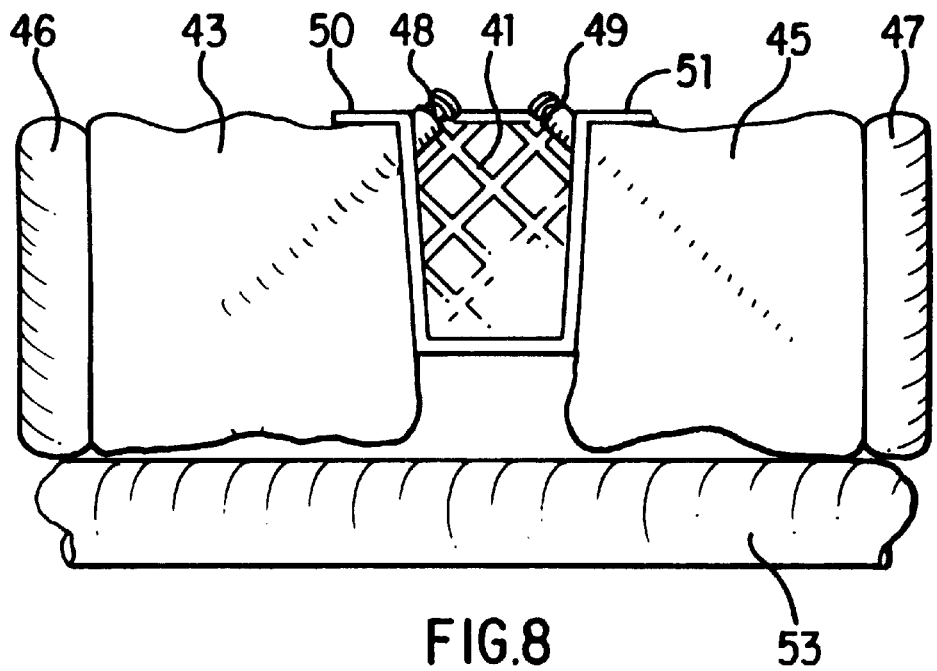
FIG. 8 provides a cross-sectional side elevational view of another alternative embodiment of the present invention.
Figure 9:
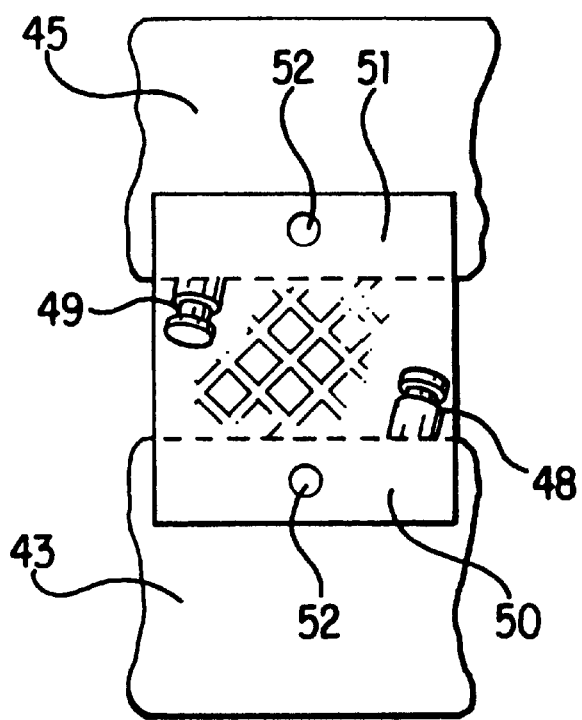
FIG. 9 provides a top view of the device shown in FIG. 8.

FIGS. 8 and 9 show another alternative embodiment, which is intended for use in filling the space between adjacent vertebral bodies following removal of an intervertebral disc. Mesh cage 41 sits between vertebral bodies 43 and 45. Intervertebral discs 46 and 47 flank the vertebral bodies. The spinal cord is indicated by reference numeral 53. Cage 41 fills the space previously occupied by another such disc. The cage includes barrel vaults 48 and 49, and has flanges 50 and 51 which help to anchor the cage on the vertebral bodies and provide means for attachment thereto. The flanges also prevent the cage from being inadvertently tapped into the spinal cord, and they also distribute the shear and bending moment and thus increase the stability of the device. The flanges also provide one or more additional holes to accommodate more screws for affixing the device to the vertebral bodies. Both the flanges and barrel vaults are preferably integral with the cage. The barrel vaults can be either threaded or non-threaded.

The screws which are inserted through the barrel vaults are preferably of the locking type, so that they lock into the barrel vaults when fully inserted.

The top view of FIG. 9 shows holes 52 formed in the flanges, which holes allow additional servertebral bodies, ters to be inserted into the vertebral bodies, to provide further security for the cage. As clearly shown in FIG. 8, the cage has a trapezoidal cross-section to facilitate wedging of the device into a restricted space. The cage is preferably rectangular when viewed from the top or the bottom.

The cage may be constructed such that the bottom (the side pointed towards the spinal cord) is solid and not made of mesh. The top of the cage could also be solid. A mesh structure is most necessary on the sides of the cage, where the cage abuts the vertebral bodies, so as to promote fusion between the bone chips or bone substitute material inside the cage and the adjacent vertebral bodies.

Figure 10:
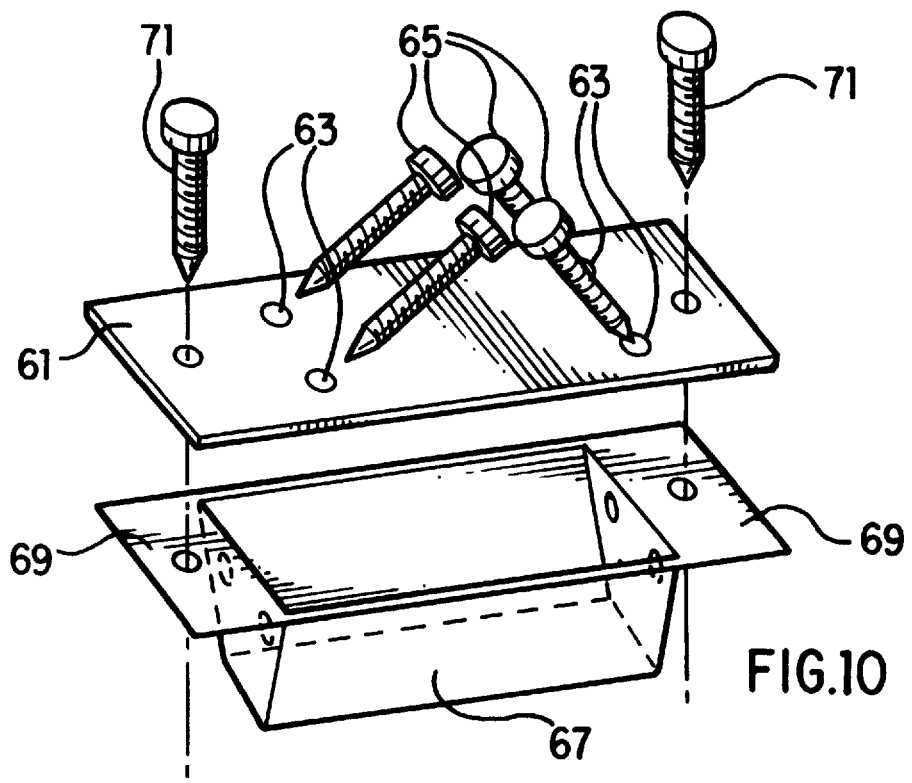
FIG. 10 provides an exploded perspective view of a non-telescoping fusion stabilization chamber having a separate top plate, according to the present invention.
Figure 11:
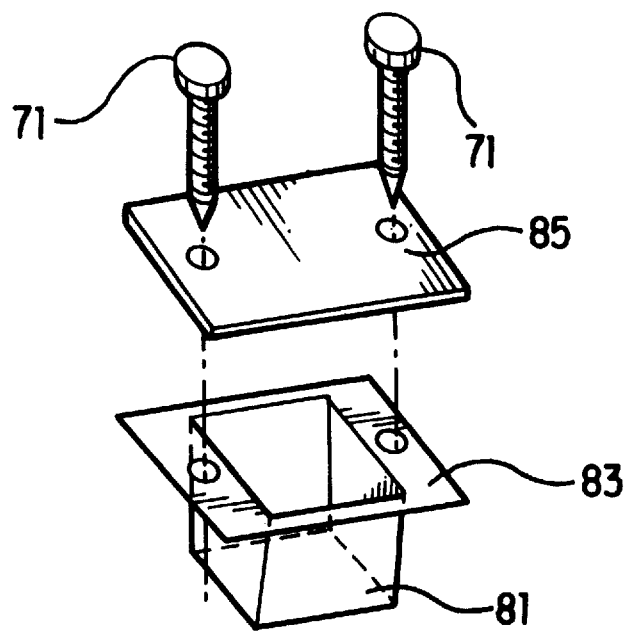
FIG. 11 provides a perspective view of a non-telescoping device having a separate top plate, which device is intended for use in filling the space between vertebrae, following removal of an intervertebral disc.

FIGS. 10 and 11 show embodiments which include separate top plates. Neither of the devices shown in FIGS. 10 and 11 has a telescoping structure. For convenience of illustration, the mesh structure of the devices is not shown in these figures. The device of FIG. 10 is intended to fill the space of a removed vertebral body, or the like, and the smaller device of FIG. 11 is intended to fill the space created by removal of an intervertebral disc.

In the embodiment of FIG. 10, top plate 61 has holes 63 which are oriented such that screws 65 can be inserted in a mutually oblique orientation. Thus, holes 63 perform the function of the barrel vaults in the other embodiments. The chamber 67 preferably has a trapezoidal cross-section. It also has flanges 69 to facilitate anchoring to adjacent vertebrae. Screws 71 fit through suitable holes in the top plate and flanges to provide additional means for affixing the top plate to the flanges, and for anchoring the entire device in place.

In the embodiment of FIG. 11, chamber 81 has an attached pair of flanges 83. A separate top plate is attached to the chamber by screws, similar to the manner of FIG. 10. The same screws that hold the top plate to the body of the chamber also hold the entire device to adjacent vertebrae. The major difference between the embodiment of FIG. 11 and that of FIG. 10 is in size; the embodiment of FIG. 11 is smaller because it is intended for filling the space created by removal of an intervertebral disc.

Any of the embodiments of FIGS. 8–11 can be made with the curved shape illustrated in FIG. 7.

Figure 12:
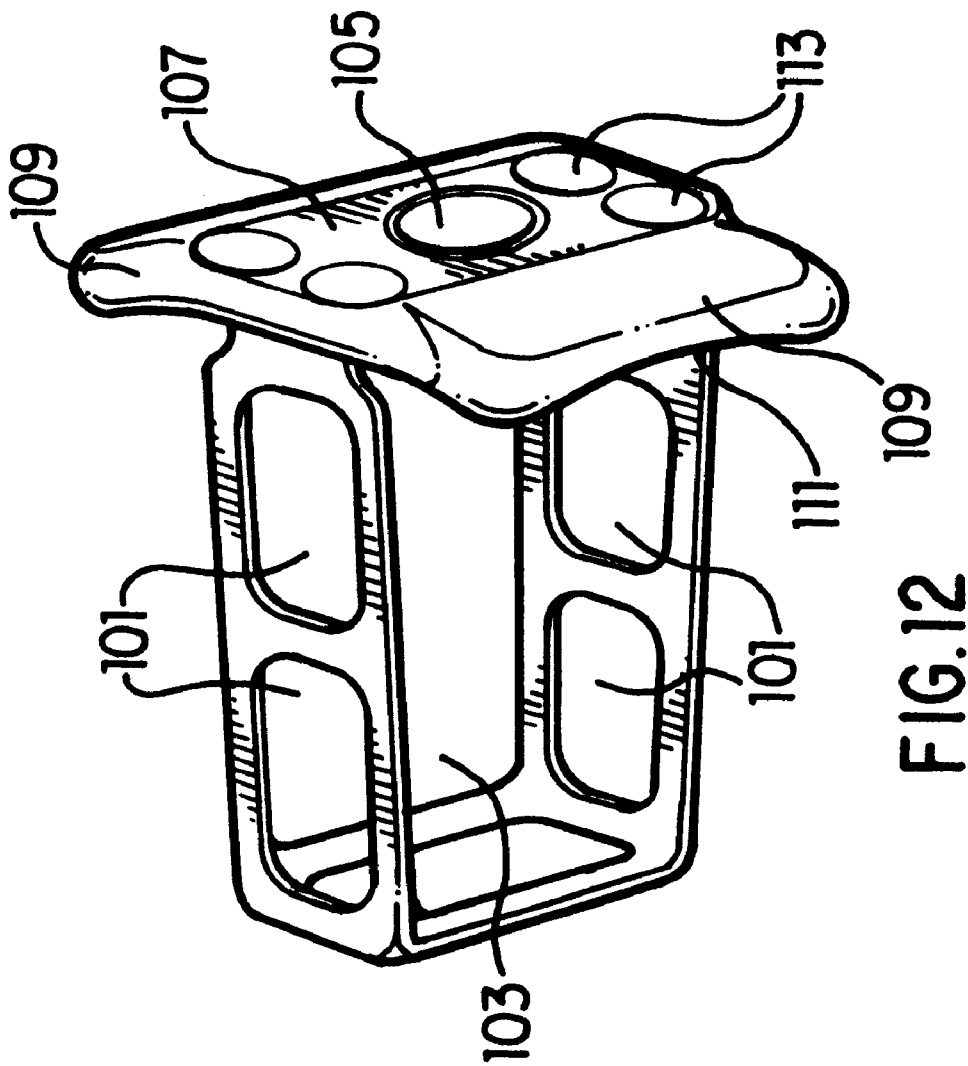
FIG. 12 provides a perspective view of a fusion stabilization chamber made according to another embodiment of the present invention.

FIG. 12 provides a perspective view of a fusion stabilization chamber made according to another alternative embodiment of the present invention. FIG. 12 shows the chamber with relatively large holes or slots 101. These large slots themselves can comprise a mesh structure, if the bone pieces to be inserted into the chamber are sufficiently large that these slots will contain the pieces. Alternatively, the slots could be made somewhat smaller, so that they can hold bone pieces that are somewhat smaller. In still another alternative, the large slots shown in FIG. 12 can be covered over with the same mesh structure shown in FIGS. 1–7. The latter arrangement is useful when the bone pieces to be held in the chamber are much smaller. All of these arrangements are within the scope of the present invention. The term "mesh structure", as used in this description, is therefore intended to include all of these arrangements.

Subject to the requirement that the mesh structure be capable of containing the bone fragments, it is desirable to make the openings of the mesh structure as large as possible, to allow bone to grow through the mesh. Thus, the mesh structure should be fine enough to contain bone fragments, but coarse enough to allow bone to grow through the mesh. The bone fragments are placed in empty space 103. The bone material can be conveniently introduced through access hole 105 formed in end portion 107.

The end portion defines flanges 109. The flanges have curved portions 111 which are shaped to correspond to the curvature of surrounding vertebrae, as will be apparent in the subsequent figures. The curved portions thereby enhance the stability of the device while it is situated between vertebrae. Holes 113 allow bone screws, or their equivalent, to be inserted through the end portion 107 and into surrounding bone.

The fusion stabilization chamber of FIG. 12, like those shown in the other embodiments, is free of sharp protrusions. That is, as illustrated in FIG. 12, while the structural elements defining the chamber do have corners, they do not include protrusions which could, intentionally or unintentionally, engage the surrounding bone or tissue. Unlike many prior art devices, there is nothing in the structure of the present invention which inherently tends to grasp or prick the surrounding bone. Instead, the device is attached to the adjacent bone primarily due to the fact that it has a trapezoidal shape, in at least two mutually-orthogonal directions, so that the device wedges snugly between vertebrae. In addition, the bone screws, which fit through holes 113, prevent the device from rotating or translating while in place. It is important to make the chamber free of sharp protrusions, to avoid damage to nerves and other tissues during and after insertion.

Figure 13A:
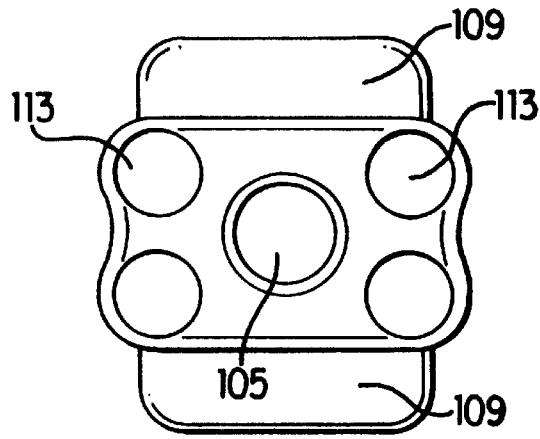
FIG. 13a provides an end view of the fusion stabilization chamber of FIG. 12.
Figure 13B:
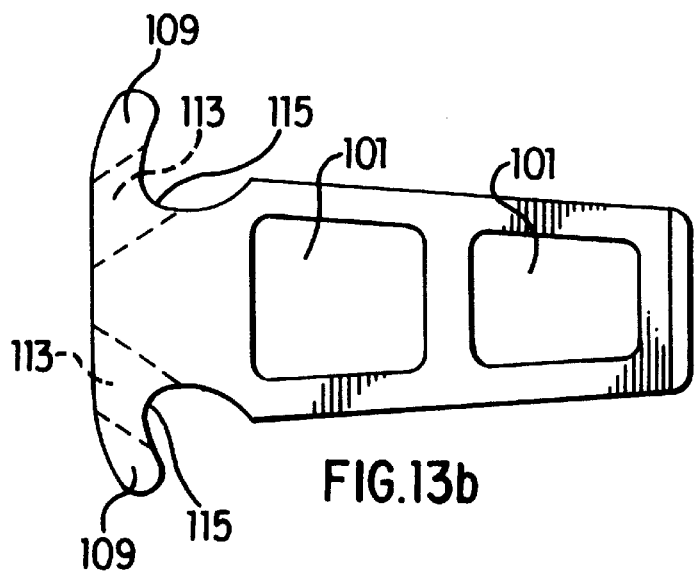
FIG. 13b provides a side view of the fusion stabilization chamber of FIG. 12.
Figure 13C:
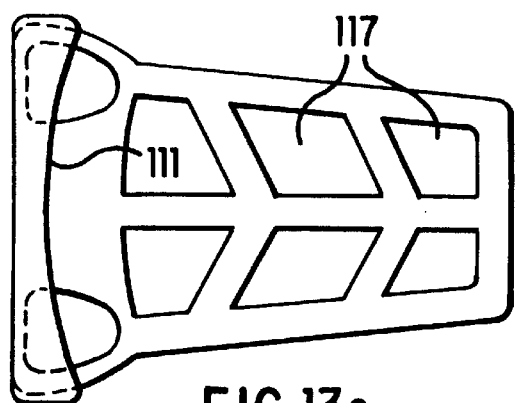
FIG. 13c provides a top view of the fusion stabilization chamber of FIG. 12.

FIGS. 13a–13c provide end, side, and top views, respectively, of the fusion stabilization chamber of FIG. 12. In all of FIGS. 12–16, similar elements have been designated with similar reference numerals. The top view depicted in FIG. 13c shows that the slots 117 on the top and bottom have a different shape from those of the side walls (which are shown in FIG. 13b and FIG. 12). However, the shape of the slots can be varied, and is not intended to limit the invention. For simplicity of illustration, the configuration of the top and bottom walls is not shown in FIG. 12, it being understood that these walls could have the configuration shown in FIG. 13c. FIG. 13b also shows notches 115 which assist in anchoring the device between vertebrae, as will be described below. The notches are defined primarily by the chamber, and in part by the flanges, as shown in the figures.

The fusion stabilization chamber of the embodiment of FIG. 12 has the feature that it is trapezoidal in cross-section, when viewed from any of its three principal axes. This feature is best shown in FIGS. 14–16, wherein it is apparent how each trapezoidal shape enables the device to perform its desired function.

Figure 14:
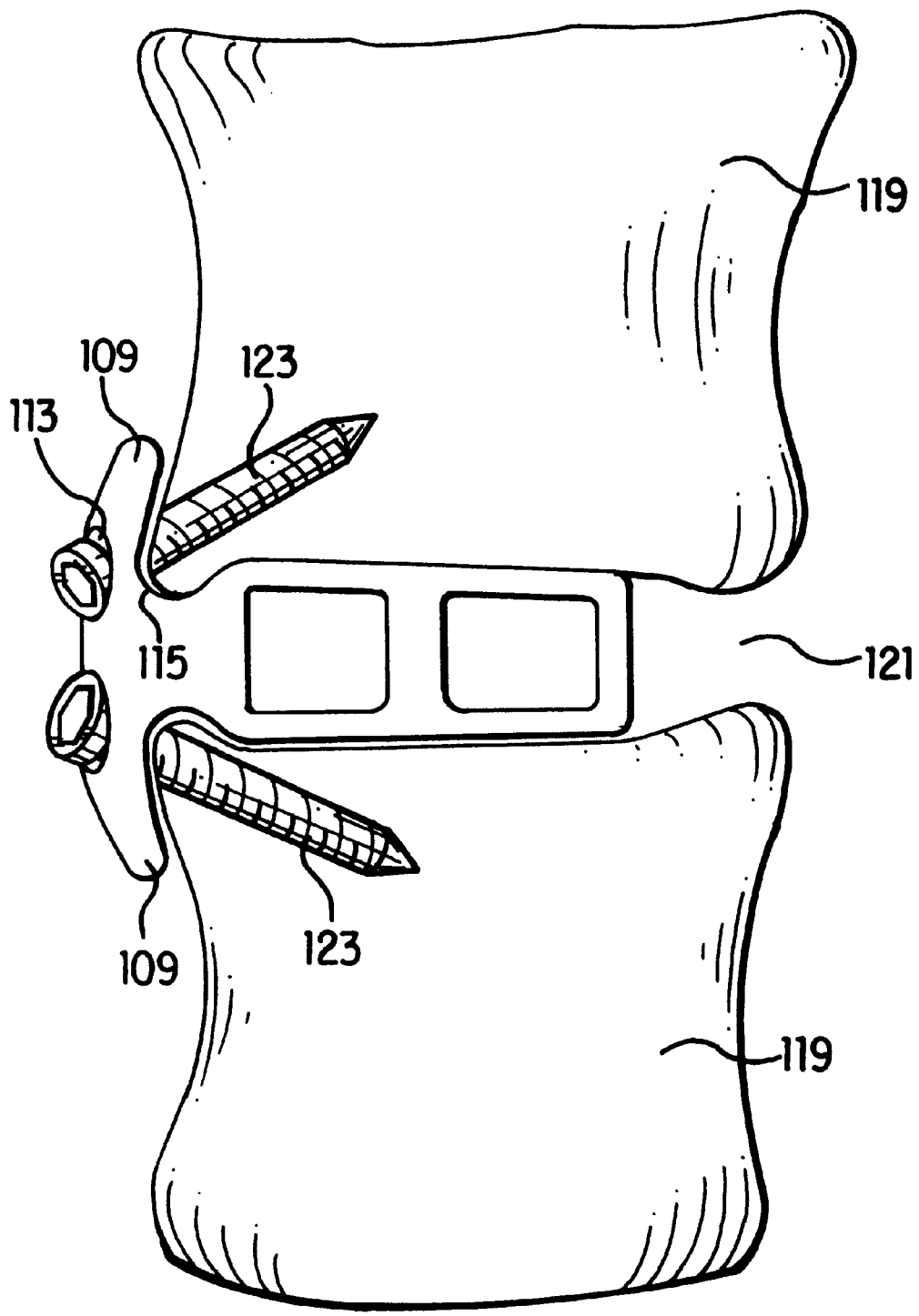
FIG. 14 provides a coronal, or antero-posterior view of the fusion stabilization chamber of FIG. 12 inserted between vertebrae.

FIG. 14 shows the fusion stabilization chamber of FIG. 12 inserted between adjacent lumbar vertebrae, in a coronal, or antero-posterior, view. Lumbar vertebrae 119 surround lumbar disc space 121, into which the device of the present invention is inserted. FIG. 14 shows how the flanges 109 and the notches 115 cooperate to engage the corners of the vertebrae. The figure also shows bone screws 123 inserted through holes 113 so that the device is firmly anchored to the vertebrae. The chamber has a trapezoidal shape, with the height of the wall decreasing slightly as one proceeds to the right in FIG. 14. The trapezoidal nature of the chamber may be very slight, in that the difference in heights of the wall at the left and right sides may be small, as shown in the figure.

Figure 15:
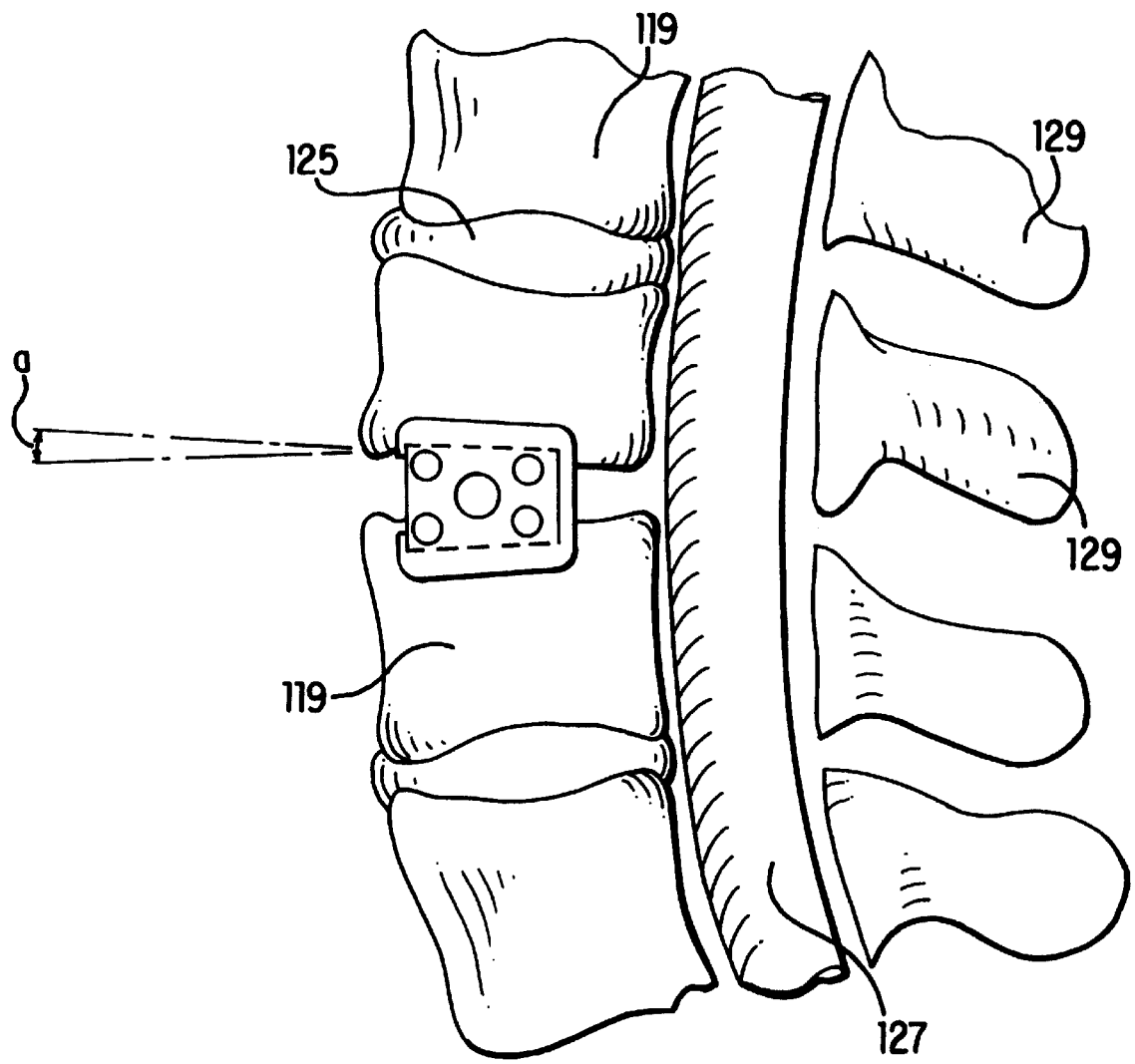
FIG. 15 provides a sagittal view of the fusion stabilization chamber of FIG. 12 inserted between vertebrae.

The sagittal view of FIG. 15 shows the same device inserted between lumbar vertebrae, except that one sees the end of the device instead of its side. In this view, one sees the lumbar vertebrae 119, and a lumbar disc 125. The figure also shows the dural sac 127, which contains neural elements, and the spinous processes 129. The device still has a trapezoidal shape when viewed in the illustrated direction (which is orthogonal relative to the direction indicated in FIG. 14). Thus, the height of the device illustrated in FIG. 15 decreases as one proceeds to the right in the figure. The trapezoidal shape in this direction assists in restoring the lordotic angle a.

Figure 16:
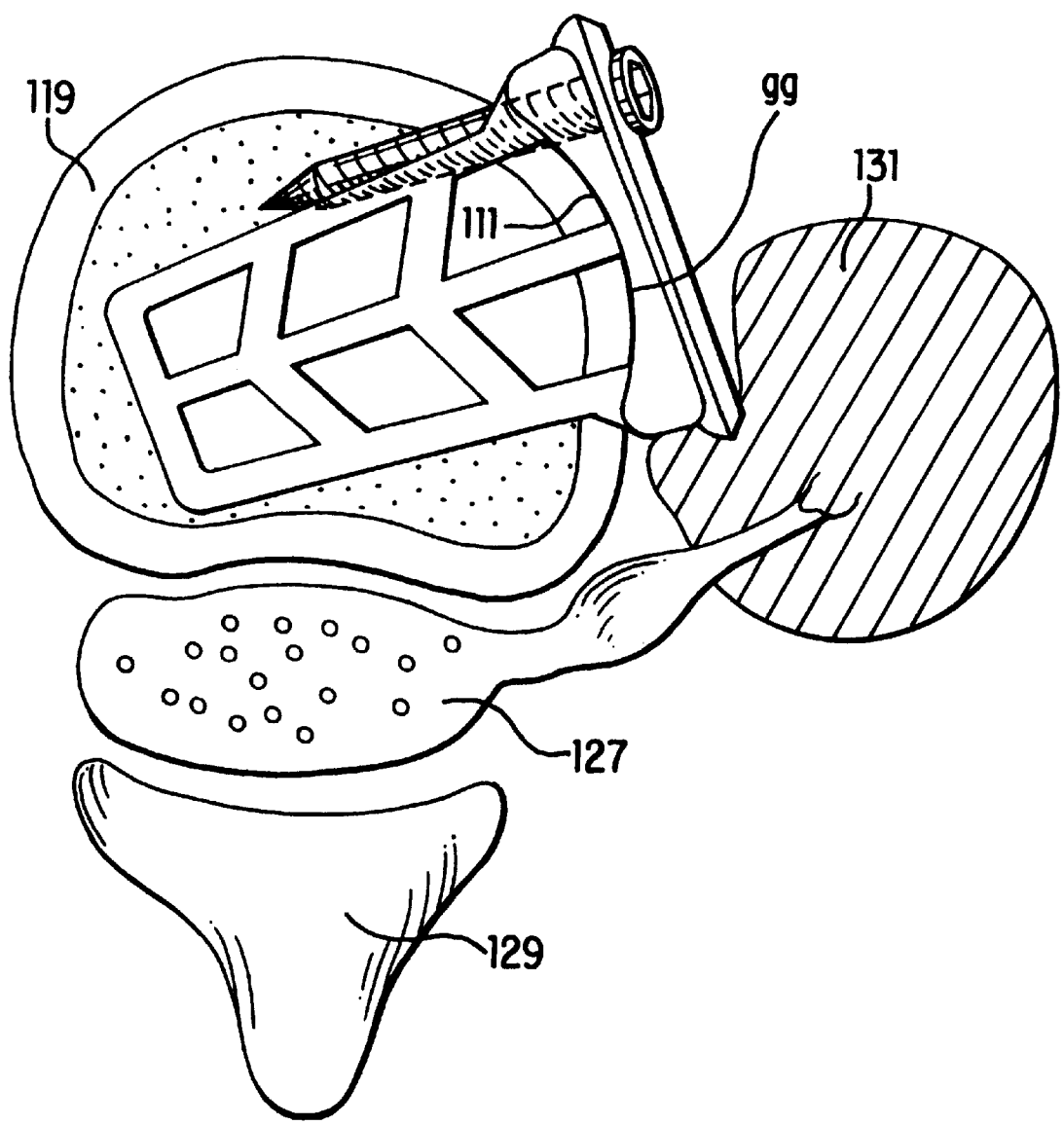
FIG. 16 provides an axial cross-sectional view showing the fusion stabilization chamber of FIG. 12 inserted between vertebra.

The axial cross-sectional view of FIG. 16 shows the same device from a different perspective. This figure takes a slice through the vertebra, and shows the same fusion stabilization chamber which is sandwiched between adjacent vertebrae. For clarity of illustration, the figure omits the vertebra on top, i.e. the vertebra which, if shown, would hide the chamber. FIG. 16 also shows the psoas muscle 131 located adjacent to the vertebrae. As in the preceding figures, the chamber in this figure has a trapezoidal shape. FIG. 16 also shows how the curved portion 111 of the flange engages the curved outer surface of the vertebra. Because it has a shape which generally corresponds to the adjacent vertebra, the curved portion of the flange enhances the stability of the device.

FIGS. 14–16 show that the embodiment of FIG. 12 is trapezoidal (or slightly trapezoidal) when viewed in cross-section in each of three mutually-orthogonal directions.

FIGS. 14–16 also illustrate the fact that the device contacts the surrounding bone along four planar surfaces, as well as at the two notches and along the two curved surfaces. The use of multiple planar surfaces which directly contact the surrounding vertebrae adds considerable stability to the device.

Although the embodiment of FIG. 12 has been described with respect to the lumbar vertebrae, it should be understood that the device can be used with other vertebrae, such as cervical vertebrae, with minor modifications. Among other things, a fusion stabilization chamber inserted between cervical vertebrae would be smaller than that used with lumbar vertebrae. Also, when used for the cervical vertebrae, the device would preferably not be trapezoidal when observed in the end view, but instead would be square or rectangular in that direction. The device used for the cervical vertebrae would be inserted from the front, whereas the device used for the lumbar vertebrae would be inserted from the side.

Thus, in the most general case, the device of the present invention has a trapezoidal cross-section when viewed in at least two mutually-orthogonal directions.

The embodiment of FIG. 12 is not limited by the material used to make the chamber or to make the mesh. The same wide variety of materials used in the other embodiments can be used in this embodiment also.

While the above description illustrates the preferred embodiments of the invention, one can vary the invention in still other ways. For example, as noted above, one can vary the structure of the walls of the chamber. While one prefers a chamber having holes, such as provided by a metal mesh, one could use an empty box having solid walls. The position and number of barrel vaults can also vary. The mesh itself need not be metal, but can be made of a plastic, preferably a biodegradable compound. These and other modifications, which those skilled in the art will recognize, should be considered within the spirit and scope of the following claims.

What is claimed is:

1. A fusion stabilization chamber, comprising;
    a) a hollow member comprising an intervertebral spacer, the hollow member having a length and a longitudinal axis,
    b) the hollow member having an end portion, the end portion defining at least one hole for receiving a screw for affixing the hollow member to a surrounding bone, the end portion including at least one flange, the flange being monolithic with the hollow member, wherein the flange has a curved portion, the curved portion being shaped to correspond to a curved surface of a surrounding bone,
    wherein the flange has a length which is less than the length of the hollow member,
    wherein the hole is oblique relative to the longitudinal axis of the hollow member, and
    wherein the hollow member has, a body portion, adjacent to said end portion, the body portion having an exterior wall which tapers down linearly, free of protrusions, from a greater width, adjacent to the end portion, to a lesser width at a position opposite to the end portion.

2. The fusion stabilization chamber of claim 1, wherein the hollow member includes at least one wall defined by a mesh, the hollow member being substantially filled with a material selected from the group consisting of bone chips, bone substitutes, and bone forming substrates having bone morphogenic proteins, and combinations of the above, and wherein the mesh defines openings sufficiently large to allow the material located within the hollow member to fuse with bone material located outside the hollow member.

3. The fusion stabilization chamber of claim 1, wherein the hollow member defines at least one notch which is shaped to engage an edge of a surrounding bone.

4. The fusion stabilization chamber of claim 1, wherein the hollow member has a trapezoidal cross-section when viewed in each of at least two mutually-orthogonal directions.

5. The fusion stabilization chamber of claim 1, wherein the end portion includes an access hole, the access hole comprising means for filling the hollow member with bone fragments.

6. The fusion stabilization chamber of claim 1, wherein the hollow member is free of any sharp protrusions.

* * * * *